(12) United States Patent
Marceaux et al.

(10) Patent No.: US 11,464,642 B2
(45) Date of Patent: Oct. 11, 2022

(54) TIBIAL COMPONENT AND TIBIAL INSERT OF A KNEE PROSTHESIS COMPRISING A PROMONTORY AND ITS ASSOCIATED CUT-OUT

(71) Applicant: X.NOV IP, Luxembourg (LU)

(72) Inventors: Pascal Marceaux, Chaumont (FR);
Jean-François Biegun, Boncourt (CH);
Frédérique Biegun, Boncourt (CH);
Pascal Loehle, Bressaucourt (CH);
Damien Arnalsteen,
Coudekerque-Branche (FR)

(73) Assignee: X.NOV IP, Luxembourg (LU)

( * ) Notice: Subject to any disclaimer, the term of this patent is extended or adjusted under 35 U.S.C. 154(b) by 0 days.

(21) Appl. No.: 17/256,699

(22) PCT Filed: Jul. 8, 2019

(86) PCT No.: PCT/EP2019/068242
§ 371 (c)(1),
(2) Date: Dec. 29, 2020

(87) PCT Pub. No.: WO2020/011705
PCT Pub. Date: Jan. 16, 2020

(65) Prior Publication Data
US 2021/0369464 A1      Dec. 2, 2021

(30) Foreign Application Priority Data

Jul. 12, 2018 (FR) ...................................... 18 70828

(51) Int. Cl.
*A61F 2/38* (2006.01)
*A61F 2/30* (2006.01)

(52) U.S. Cl.
CPC ............ *A61F 2/389* (2013.01); *A61F 2/3886* (2013.01); *A61F 2002/305* (2013.01); *A61F 2002/30429* (2013.01)

(58) Field of Classification Search
CPC ....... A61F 2/389; A61F 2/3859; A61F 2/3868
See application file for complete search history.

(56) References Cited

U.S. PATENT DOCUMENTS

| | | | |
|---|---|---|---|
| 2011/0082559 A1 | 4/2011 | Hartdegen et al. | ......... 623/20.32 |
| 2012/0035735 A1 | 2/2012 | Sanford et al. | ........... A61F 2/38 |
| 2013/0184829 A1 | 7/2013 | Wyss et al. | ............... A61F 2/38 |

FOREIGN PATENT DOCUMENTS

| | | | | |
|---|---|---|---|---|
| EP | 0 636 352 A2 | 2/1995 | ............... | A61F 2/38 |
| WO | WO 2017/155995 A1 | 9/2017 | ............... | A61F 2/38 |

OTHER PUBLICATIONS

International Search Report dated Oct. 1, 2019 in related application No. PCT/EP2019/068242.

*Primary Examiner* — Jason-Dennis N Stewart
(74) *Attorney, Agent, or Firm* — Renner, Kenner, Greive, Bobak, Taylor & Weber

(57) ABSTRACT

A tibial component of a knee prosthesis includes a tibial plate and a tibial insert, and anterior and posterior abutments projecting from an upper face of the tibial plate. The anterior abutment extends along at least part of the tibial plate and the posterior abutment extends for at least part of the tibial plate and comprises a part forming a promontory and an anterior cut-out, in particular central, in the form of a window formed in the anterior abutment opening onto the posterior face of the latter opposite the part forming the promontory. The tibial insert has a face upper, a face lower and a lateral face, which has a shape matching the part forming the promontory, characterised in that at least one (Continued)

flexible tab in the form of a hook projects centrally from an anterior face of the insert and locks by snap-fitting, into the anterior cut-out.

16 Claims, 9 Drawing Sheets

TIBIAL COMPONENT AND TIBIAL INSERT OF A KNEE PROSTHESIS COMPRISING A PROMONTORY AND ITS ASSOCIATED CUT-OUT

CROSS-REFERENCE TO RELATED APPLICATION

This is a § 371 application of International patent application number PCT/EP2019/068242 filed Jul. 8, 2019, which claims priority of French application FR 18 70828 filed Jul. 12, 2018.

TECHNICAL FIELD

The present invention refers to a knee prosthesis comprising a tibial component, a femoral component and a tibial insert in a softer material interposed between the tibial component and the femoral component. The present invention also refers to the tibial component of a prosthesis of this type and in particular to a tibial component comprising a tibial plate and an insert intended to be fixed to the tibial plate of the tibial component in particular by a snap-fit action. The present invention also refers to a tibial insert intended to be fixed, in particular by a snap-fit action, to the tibial plate of a tibial component according to the invention.

BACKGROUND ART

Tibial prostheses are also well known from the prior art, for example from the document US 2013/0184829. Classically, the tibial prosthesis comprises a tibial component, consisting of a tibial plate and a stem intended to be anchored in the tibia to fix the tibial component to the tibia and a femoral component comprising condyles. An insert, classically of polyethylene is fitted between the tibial component and the femoral component, comprising upper surfaces intended to meet the condyles of the femoral component to permit relative flexing of the tibial component with respect to the tibial component to limit the movement of the knee. In these well-known tibial prostheses, it is known that the tibial plate comprises two distinct abutments that extend along the bounding margin of the tibial plate, that is an anterior abutment extending along at least part of the anterior margin of the tibial plate and a posterior abutment comprising a part forming a promontory extending from the posterior margin in the direction of the anterior abutment in the shape of a promontory. The tibial insert designed to work with such a tibial component contains cavities in its lower part, that is a lower anterior cut-out designed to cover the anterior abutment of the tibial plate and a lower posterior cut-out designed to cover the part forming the promontory. An anterior tab projects from the anterior face of the insert and is designed to fit by snap-action into a central cut-out facing the posterior face of the anterior abutment. The insert also comprises two posterior tabs intended to be inserted into the grooves formed in the posterior abutment. These old types of prosthesis and in particular the configurations of the tibial plate and the tibial insert to permit snap-fitting of the insert into the plate are complex structures, in particular requiring the provision of a vertical insert projecting from the insert and a corresponding hole formed in the plate. The present invention aims to overcome the problems associated with the older types by proposing a tibial plate, a tibial insert and an assembly consisting of a tibial plate and a tibial insert that ensures improved fixing with respect to the older type, in particular by snap-fitting the insert to the plate, while being a simpler structure, in particular not requiring the provision of a vertical insert projecting from the insert with a corresponding hole formed in the plate.

SUMMARY OF THE INVENTION

According to one aspect of the invention, a tibial component of a total knee prosthesis is as defined in claim 1.

This aspect of the invention also refers to a tibial plate for the tibial component of a total knee prosthesis comprising means for anchoring, in particular in the form of a stem projecting from the lower face, at least two distinct abutments, anterior and posterior respectively, projecting from the upper face, the anterior abutment extending along at least part of the anterior margin of the tibial plate and the posterior abutment extending along at least part of the posterior margin of the tibial plate and comprising a part forming a promontory extending along the posterior margin in the direction of the anterior abutment in the shape of a promontory and a central, anterior cut-out in the form of a window formed in the anterior abutment opening onto the posterior face opposite to the part forming the promontory, the part forming the promontory being symmetrical with respect to the Antero-Posterior (AP) or sagittal axis.

This aspect of the invention also refers to a tibial insert for the tibial component of a knee prosthesis having an upper face (23), a lower face (22) and a lateral face, the lateral face comprising an anterior face, a posterior face and two faces on the lateral and medial side respectively, a posterior cut-out (26; 26') in the insert open on the top and on the posterior side formed in the lower face, the posterior cut-out being bounded by an anterior face set back with respect to the posterior face of the insert and having a region of a shape matching the part forming the promontory, characterised in that at least one flexible tab, in particular in the shape of a hook, projects from the insert on the anterior side, in particular centrally, so that it is able to lock, in particular by snapping fitting, into an anterior cut-out (11) in the form of a window in the tibial component.

According to another aspect of the invention, independent of the above first aspect but which can work equally well in combination with it, a tibial plate of the tibial component of a total knee prosthesis comprising means for anchoring, for example a fixing stem, the stem projecting from the lower face of the tibial plate, while at least two distinct abutments, anterior and posterior respectively, project from the upper face of the tibial plate, the anterior abutment extending along at least part of the anterior margin of the tibial plate and the posterior abutment extending along at least part of the posterior margin of the tibial plate and comprising a part forming a promontory extending, preferably centrally along the sagittal axis of the posterior margin in the direction of the anterior abutment and having the shape of a promontory, and two low posterior walls extending along the posterior margin of the tibial plate on each side of the part forming the promontory, two respective posterior grooves formed in the anterior side of the two posterior walls and a central anterior cut-out in the form of a window formed in the anterior abutment opening onto its posterior face opposite the part forming the promontory and the part forming the promontory being elongated in the sagittal direction, meaning that its greatest dimension in the sagittal or antero-posterior direction, is greater than its greatest dimension in the medio-lateral direction, characterised in that the opening margin of the central anterior cut-out defines a first plane, in particular a plane parallel to the medio-lateral axis, in particular a vertical plane perpendicular to the antero-posterior axis and the two posterior grooves extending parallel to the first plane.

This other aspect of the invention also refers to a tibial insert having an upper face, a lower face and a lateral face, the lateral face comprising an anterior face, a posterior face and two margin faces, lateral and medial respectively, and a posterior cut-out in the insert opening at the base on the posterior side being formed on the lower face and bounded by an anterior face set back with respect to the posterior face of the lateral face of the insert, the posterior cut-out in the insert having a region of a complementary shape to a part forming a promontory having a shape elongated in the sagittal direction, that is to say its greatest dimension in the sagittal or antero-posterior direction is greater than its greatest dimension in the medio-lateral direction, an flexible tab in the form of a hook projecting from one face of the insert, on the anterior side, and two posterior ribs projecting from the anterior face on each side medially and laterally from the region in the complementary shape of the part forming a promontory, the part of the face of the insert from which the flexible tab extending in a first plane, in particular a plane parallel to the media-lateral axis, in particular a plane normal and/or perpendicular to the antero-posterior axis and the two posterior ribs extending parallel to the first plane, in particular in a straight line.

The above aspect of the invention also relates to a tibial component comprising the insert and plate defined above.

According to yet another aspect of the invention, independent of the other aspects, which works equally well in combination with one or more of the other aspects, a tibial plate of the tibial component of a total knee prosthesis comprises means for anchoring, for example an anchor stem, the stem projecting from the lower face of the tibial plate, while at least two distinct abutments, anterior and posterior respectively, project from the upper face of the tibial plate, the anterior abutment extending along at least part of the anterior margin of the tibial plate and the posterior abutment extending along at least part of the posterior margin of the tibial plate and comprising a part forming a promontory extending, preferably centrally, along the sagittal axis from the posterior margin in the direction of the anterior abutment and having the shape of a promontory, at least one anterior cut-out, in particular a central cut-out, preferably in the form of a window, being formed in the anterior abutment opening onto its posterior face, in particular opposite the part forming the promontory, characterised in that the posterior face of the anterior abutment comprises a central section extending in a first plane, in particular parallel to the media-lateral axis, and preferably vertical, and two end sections, lateral and medial respectively, that extend in the respective planes, in particular vertical, that form respective angles with respect to the first plane that are less than 180°, in particular between 135° and 175°, and in particular between 150° and 160°.

This yet further aspect of the invention also relates to a tibial insert having an upper face, a lower face and a lateral face, the lateral face comprising an anterior face, a posterior face and two side faces, lateral and medial respectively, an anterior cut-out in the insert formed in the lower face of the insert, on the anterior side, this anterior cut-out in the insert being bounded by a posterior face and an upper face, being open on the anterior side and on the top, and a posterior cut-out in the insert open on the top and on the posterior side being formed in the lower face and bounded by an anterior face set back with respect to the posterior face of the insert, the posterior cut-out in the insert having a region in a shape that matches the part forming the promontory, in particular a part forming the promontory having an elongated shape in the sagittal direction, that is to say its greatest dimension in the sagittal or antero-posterior direction, is greater than its greatest dimension in the medio-lateral direction, the posterior face of the anterior cut-out in the insert comprising a central section extending in a first plane parallel to the medio-lateral axis, preferably vertical, and two end sections, lateral and medial respectively, that extend in their respective planes, in particular vertical, forming an angle with respect to the first plane that is greater than 180°, in particular between 185° and 225°, and in particular between 200° and 210°.

The above aspect of the invention also relates to a tibial component comprising the insert and plate defined above.

According to yet another aspect of the invention, independent of the other aspects, but which works equally well in combination with one or more of the other aspects, a tibial plate of the tibial component of a total knee prosthesis comprises means for anchoring, for example an anchor stem, the stem projecting from the lower face of the tibial plate, while at least two distinct abutments, anterior and posterior respectively, project from the upper face of the tibial plate, the anterior abutment extending along at least part of the anterior margin of the tibial plate and the posterior abutment extending along at least part of the posterior margin of the tibial plate and comprising a part forming a promontory extending, preferably centrally along the sagittal axis, from the posterior margin in the direction of the anterior abutment in the form of a promontory, and at least one anterior cut-out, in particular central, formed in the anterior abutment and opening onto its posterior face, in particular opposite the part forming the promontory, characterised in that the part forming the promontory has a shape elongated in the sagittal direction, that is to say that its greatest dimension on the sagittal or antero-posterior direction, is greater than its greatest dimension in the medio-lateral direction and one or more vertical ribs project from at least one of the lateral faces of the medial and lateral sides of the promontory, in particular from each of the lateral faces of the medial and lateral sides.

This yet further aspect of the invention also relates to a tibial insert with an upper face, a lower face and a lateral face, the lateral face comprising an anterior face, a posterior face and two side faces, lateral and medial respectively, a posterior cut-out in the insert open at the top and posterior side formed in the lower face of the insert and bounded by an anterior face set back to the posterior face of the insert, the posterior cut-out in the insert having a region of a shape of matching the part forming the promontory, a shape elongated in the sagittal direction, that is to say the greatest dimension in the sagittal or antero-posterior direction is greater than its greatest dimension in the medio-lateral direction, and it is formed in the anterior face of the posterior cut-out of the insert, in the matching region of the part forming the promontory, vertical grooves, and at least one flexible tab in the form of a hook projecting from the posterior face of the insert, in particular centrally.

The above aspect of the invention also relates to a tibial component comprising the insert and plate defined above.

Yet another aspect of the invention, independent of the other aspects, but which works equally well in combination with one or more of the other aspects, relates to the tibial plate of a tibial component of a total knee prosthesis comprising means for anchoring, in particular in the form of a stem projecting from the lower face of the tibial plate, at least two distinct abutments, anterior and posterior respectively, projecting from the upper face of the tibial plate, the anterior abutment extending along at least part of the anterior margin of the tibial plate and the posterior abutment extending along at least part of the posterior margin of the tibial plate and comprising a part forming a promontory (14; 14'; 14") extending from the posterior margin in the direction of the anterior abutment and in the shape of a promontory and an anterior cut-out (11) in the form of a window formed in the anterior abutment (4; 4') opening from its posterior face (7; 7') opposite the part (14; 14'; 14") forming the promontory, characterised in that the part (14; 14'; 14") forming the promontory is bounded by a lateral wall defined by two faces, medial and lateral respectively, meeting at an anterior face forming the summit, the faces of the lateral walls being straight, inclined inwards or curved so as not to present hooked upper margins.

This other aspect of the invention also relates to a tibial insert with an upper face, a lower face and a lateral face, the lateral face comprising an anterior face, a posterior face and two side faces, lateral and medial respectively, a posterior cut-out in the insert open at the top and posterior side formed in the lower face of the insert and bounded by an anterior face set back with respect to the posterior face of the insert and two faces, medial and lateral respectively, meeting at the anterior face, the medial and lateral faces and the anterior face of the posterior cut-out of the insert being straight, inclined inwards or so as not to present hooked upper margins.

The above aspect of the invention also relates to a tibial component comprising the insert and plate defined above.

Yet another aspect of the invention, independent of the other aspects, but which works equally well in combination with one or more of the other aspects, relates to the tibial plate of a tibial component of a total knee prosthesis comprising means for anchoring, in particular in the form of a stem projecting from the lower face of the tibial plate, at least two distinct abutments, anterior and posterior respectively, projecting from the upper face of the tibial plate, the anterior abutment extending along at least part of the anterior margin of the tibial plate and the posterior abutment extending along at least part of the posterior margin of the tibial plate and comprising a part forming a promontory (14; 14'; 14") extending from the posterior margin in the direction of the anterior abutment in the form of a promontory, and an anterior cut-out (11) in the form of a window formed in the anterior abutment (4; 4') opening from its posterior face (7; 7') opposite the part (14; 14'; 14") forming the promontory, characterised in that the part (14; 14'; 14") forming the promontory has an elongated shape, that is to say that its greatest length, that is to say in the Antero-Posterior, or AP, direction is greater than its greatest width, that is to say in the ML (or medio-lateral) direction, and the part forming the promontory is symmetrical about the AP axis.

This other aspect of the invention also relates to a tibial insert with an upper face, a lower face and a lateral face, the lateral face comprising an anterior face, a posterior face and two side faces, lateral and medial respectively, a posterior cut-out in the insert open at the top and posterior side formed in the lower face of the insert and bounded by an anterior face set back with respect to the posterior face of the insert, the posterior cut-out in the insert having a region of matching shape on one side forming a promontory with an elongated shape, that is to say that the greatest length, that is to say in the Antero-Posterior, or AP direction, is greater than its greatest width, that is to say in the ML (or medio-lateral) direction and symmetrical about the AP axis.

Thus, according to the various aspects of the invention, locking is obtained, in particular by snap fitting, which holds the tibial insert into the tibial plate perfectly with only a simple structure.

Preferably, the part forming the promontory is in at least one sagittal segment along the sagittal direction in the form of a truncated cone, that is to say that its width, measured in the medio-lateral direction, decreases along at least one segment running in the sagittal direction towards the anterior abutment.

Preferably, the part forming a promontory has a shape elongated in the sagittal direction, that is to say that the greatest dimension in the sagittal or antero-posterior direction is greater than its greatest dimension in the medio-lateral direction.

Preferably, the at least one sagittal segment extends from the posterior margin to the anterior extremity of the part forming the promontory.

Preferably, the part forming the promontory is bounded on the lateral and medial sides by two flat surfaces, preferably vertical, extending from the posterior margin and converging until they meet at their other anterior extremity at an essentially circular segment forming a summit.

According to a preferred method of implementation, the angle formed between the two flat faces of the lateral side and the medial side of the part forming the promontory is between 2° and 20°, for example between 3° and 10°.

Preferably, the posterior cut-out has a region which matches the shape of the part forming the promontory with a shape elongated in the sagittal direction, that is to say that the greatest dimension in the sagittal or antero-posterior direction is greater than its greatest dimension in the media-lateral direction.

Preferably, the matching region of the part forming the promontory is in at least one sagittal segment along the sagittal direction in the form of a truncated cone, that is to say that its width, measured in the medio-lateral direction, decreases along at least one segment running in the sagittal direction.

Preferably, an anterior cut-out in the insert is formed in the lower face of the insert, on the anterior side, this anterior cut-out in the insert being bounded by a posterior face and an upper face, that is open on the anterior side and on the top, the flexible tab being housed, at least in part, in the anterior cut-out of the insert.

Preferably, the part forming the promontory is solid and in particular does not contain a hole to accept a stem projecting from the lower face of the tibial insert.

The lateral faces of the medial side and/or the lateral side of the part forming the promontory are preferably flat.

The lateral face(s) of the medial and/or lateral side of the part forming the promontory is or are preferably vertical.

In particular, a single cut-out is provided in the posterior face of the anterior abutment.

According to a preferred method of implementation, the tibial component is symmetrical about the sagittal axis.

According to a preferred method of implementation of the invention, the central cut-out opening at the anterior face of the first anterior abutment extends over a width, measured in the media-lateral direction, which is greater than the width or the greatest width of the part forming the promontory.

It also accepts an flexible tab projecting from the lateral anterior face of the insert that is snap-fitted into this cut-out, the width of the tab being greater than the width of the promontory and the width of the posterior cavity of complementary shape of the part forming the promontory formed in the lower face of the insert.

The present invention also relates to a total knee prosthesis comprising a tibial plate according to the invention, a tibial component and a tibial insert according to the invention that is fixed, in particular by snap-fitting, to the tibial plate of the tibial component and interposed between the tibial component and the tibial component.

BRIEF DESCRIPTION OF THE DRAWINGS

As an example, the preferred methods of implementation of the invention will now be described with reference to the drawings, in which.

DETAILED DESCRIPTION OF THE INVENTION

The diagrams show various methods of implementation of a tibial component and a tibial insert of a total knee prosthesis respectively, comprising a tibial component, a femoral component and a tibial insert placed between the tibial component and the femoral component. These methods of implementation illustrate various aspects of the invention, each method of implementation incorporating one or more aspects of the invention.

Figure 1:
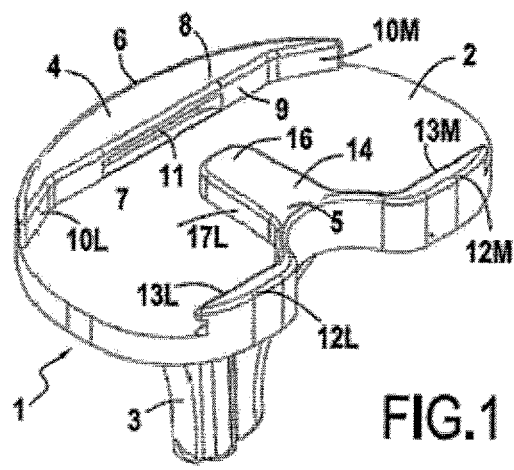
FIG. 1 is a perspective view from above of a tibial plate according to a first method of implementation of the invention.
Figure 2:
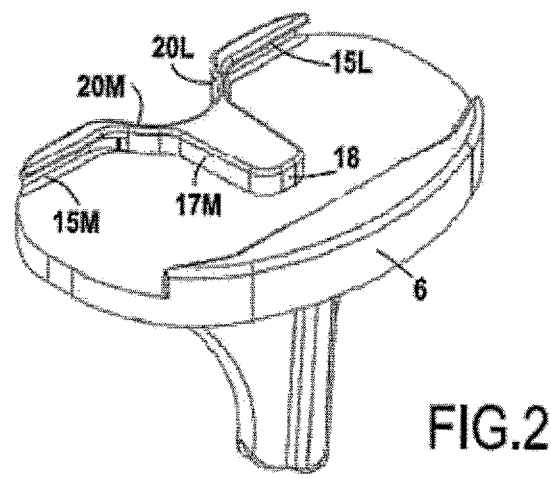
FIG. 2 is a perspective view from another angle of the tibial plate shown in FIG. 1.

In the method of implementation shown in FIGS. 1 and 2, a tibial component 1 comprises a tibial plate 2 and a stem 3 projecting from the lower face of the tibial plate 2 and designed to be anchored in the tibia to attach the tibial component to the tibia. Other methods of fixing than the insert described in FIG. 1 can be used while remaining within the scope of the present invention.

Two parts forming abutments projecting from the upper face of the tibial plate 2, namely part 4 forming the anterior abutment and part 5 forming the posterior abutment.

Part 4 forming the anterior abutment is defined by a vertical anterior face 6 extending along the inward curving anterior margin of the tibial plate 2, a posterior vertical face 7 extending further behind the interior of the plate 2 and an upper face 8 extending between the anterior and posterior faces 6 and 7. The vertical posterior face 7 of the part 4 forming the anterior abutment comprises a central region 9 and two regions 10L and 10M at the medial and lateral extremities. In the central region 9 of the part 4 forming the anterior abutment, is a central cut-out 11 in the form of a window with an opening whose peripheral margin is in the vertical plane in the form of an elongated rectangle. This cut-out 11 in the form of a window is called central because it intersects the sagittal, or antero-posterior axis, of the tibial plate, in particular it is symmetrical about this axis in being intersected by it. In particular, the central cut-out 11 in the form of a window comprises an upper margin defined by the abutment 4, this margin allowing the abutment to be hooked onto a fixing tab 29 projecting from the tibial insert described below.

The part 5 forming the posterior abutment comprises lateral and medial vertical abutments, 12L and 12M respectively, and a central part 14 in the form of a promontory that extends in the antero-posterior direction from the posterior margin of the tibial plate 2 in the direction of the part 4 forming the anterior abutment, but remaining at a distance from it. The vertical medial and lateral abutments 12L and 12M extend parallel to the medio-lateral direction along the posterior margin. Upper ledges 13L and 13M project from the anterior vertical faces of abutments 12L and 12M to define two straight, posterior grooves, 15L and 15M respectively, that extend in the medio-lateral direction in parallel with the plane in which the peripheral margin of the opening in the anterior cut-out 11 extends. The part 14 forming the promontory is bounded by two vertical faces 17L and 17M, an upper face 16 and an anterior face 18 forming a summit connecting the two faces 17L and 17M by means of rounded linking sections. The part 14 forming the promontory is linked to the two posterior abutments 12L and 12M by two vertical walls 20L and 20M forming an angle between them but not containing grooves, unlike the posterior abutments 12L and 12M.

The planes defined by the posterior faces formed by the two end regions 10L and 10M form an angle with respect to the plane defined by the central region of, for example, 150°.

In the method of implementation of FIGS. 1 to 4, the two lateral and medial faces 17L and 17 M are parallel, in particular parallel to the antero-posterior or sagittal direction.

According to another method of implementation, they may be mutually inclined, for example at an angle of between 3° and 15°, so that the part forming the promontory is in the form of a truncated cone for a segment extending from the posterior margin of the plate to the rounded junctions with the face 18 forming the summit.

Figure 3:
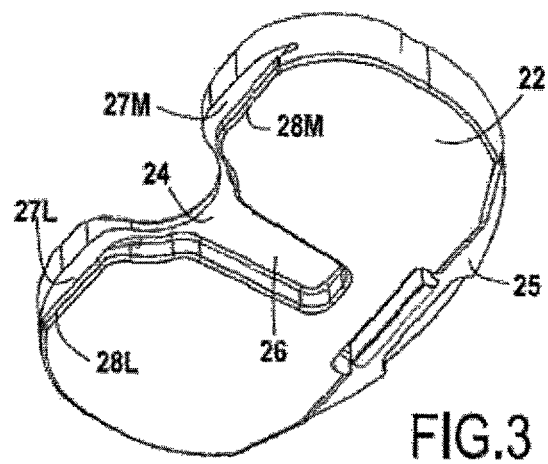
FIG. 3 is a perspective view from below of a tibial insert intended to work with the tibial plate shown in FIG. 1.
Figure 4:
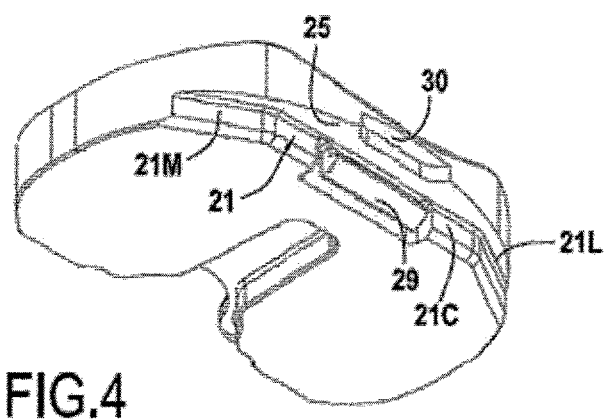
FIG. 4 is another perspective view of the tibial insert shown in FIG. 3.

FIGS. 3 and 4 show a tibial insert designed to work with the tibial component shown in FIGS. 1 and 2.

The tibial insert is classically made from a softer material than that of the tibial component, for example the tibial insert is made from polyethylene while the tibial component (like the femoral component, not shown) is made from metal. The insert has a shape that essentially matches the shape of the tibial plate 2. It is bounded by a lower face 22, an upper face 23 and a lateral face extending all around the insert between the upper and lower faces. Two cut-outs are formed in the lower face 22 of the tibial insert, posterior face 24 and anterior face 25 respectively, intended to cover the part forming the posterior abutment 5 and the part forming the anterior abutment 4 respectively. Thus the cavity 24 is open at the top and back and is bounded by an upper face and an anterior face defining a central region 26 intended to cover the part 14 forming the promontory and two lateral regions 27L and 27M intended to cover the posterior abutments 12L and 12M of the posterior abutment 5. In addition, two ribs, 28L and 28M, project from the region of the anterior face of the cut-out bounding the lateral regions 27L and 27M respectively for insertion in the grooves 15L and 15M whose shape they match. Similarly, the shape of the cavity 26 matches the part 14 forming the promontory and in particular the lateral vertical wall defining the cavity 26 matches the shape of the faces 17L, 17M and 18 of the part 14 forming the promontory.

Similarly, the shape of the lower anterior cut-out 25 of the insert matches that of the part 4 forming the anterior abutment. The cut-out 25 is open at the top and at the anterior side. An flexible tab 29 projects from the posterior vertical face 21 of the cavity 25 the head of which is intended to lock into the cut-out 11 formed in the anterior abutment 4. The width of the fixing tab 29, that is to say its dimension in the medio-lateral direction, is greater than the greatest width of region 26 of the cut-out 24 intended to cover the part 14 forming the promontory. An auxiliary anterior cut-out 30 is also formed above the cut-out 25 to assist removal by unclicking the insert from the plate. The posterior face 21 comprises a central section 21C and two end sections 21L and 21M.

The respective vertical planes defined by the end regions 21M and 21L form an angle with the vertical plane defined by the central region 21C of greater than 180°, for example 210°.

The planes defined by the end regions 21M and 21L meet in the anterior direction and diverge in the posterior direction.

According to another method of implementation, the three planes 21C, 21L and 21M can be made parallel, in particular in the medio-lateral direction, as shown in the methods of implementation shown in FIGS. 5 and 6 or 9 and 10.

The snap-fitting of the insert to the tibial component is achieved by inserting the ribs 28L and 28M into the grooves 15L and 15M respectively and inserting the part forming the promontory 14 into the region 26 by pressing downwards, then by pressing downwards again to snap fit the flexible flap of the fixing tab 29 so that the latter enters the central anterior cut-out 11 and snaps onto its upper margin, thus holding the insert to the tibial plate.

In the method of implementation shown in FIGS. 1 to 4, the upper margins of the vertical faces 17L and 17M are parallel to each other and extend in the sagittal or antero-posterior direction. In addition, the face 9 is vertical and its upper margin is straight, extending parallel to the medio-lateral axis. The two faces 10L and 10M are vertical and their upper margin is straight, forming an angle with respect to the face 9, so that the two faces 10L and 10M are oriented towards the posterior side. The faces 9, 10L and 10M thus define, from one lateral extremity to the other of the abutment 4, a posterior surface of the anterior abutment 4 which has its concave side facing in the posterior direction.

Figure 5:
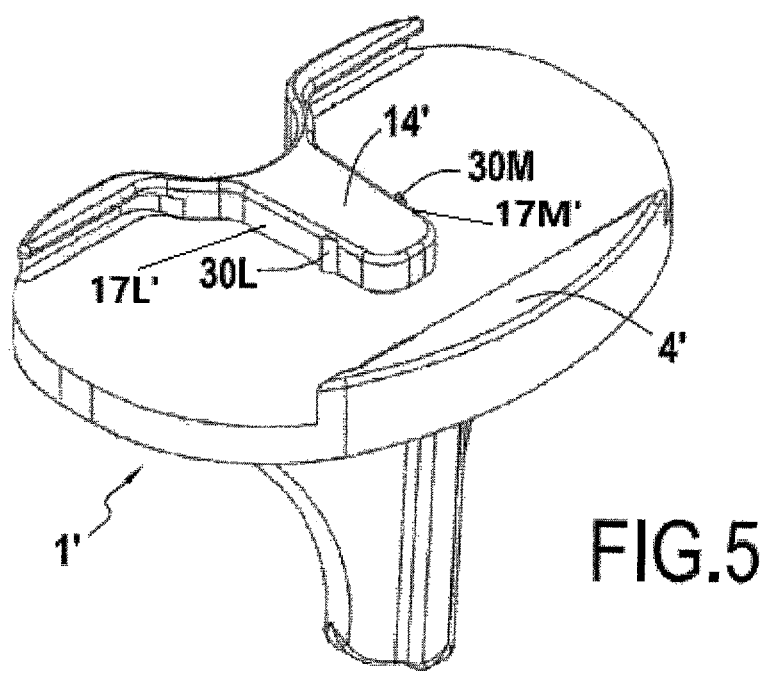
FIG. 5 is a perspective view from above of another method of implementation of a tibial plate according to the invention.
Figure 6:
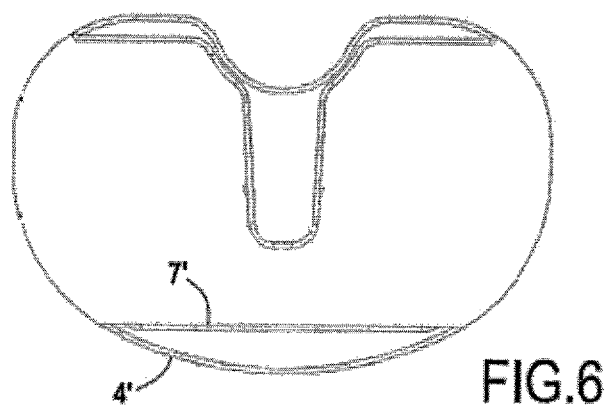
FIG. 6 is a view from above of the tibial plate shown in FIG. 5.
Figure 7:
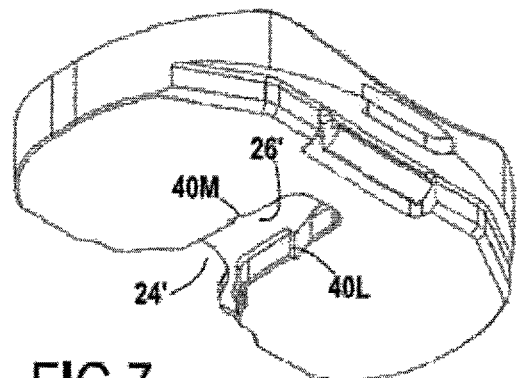
FIG. 7 is a perspective view from below of a tibial insert designed to work with a tibial plate like that shown in FIGS. 5 and 6 in which the anterior abutment has been replaced by the anterior abutment of the plate shown in FIGS. 1 and 2.
Figure 8:
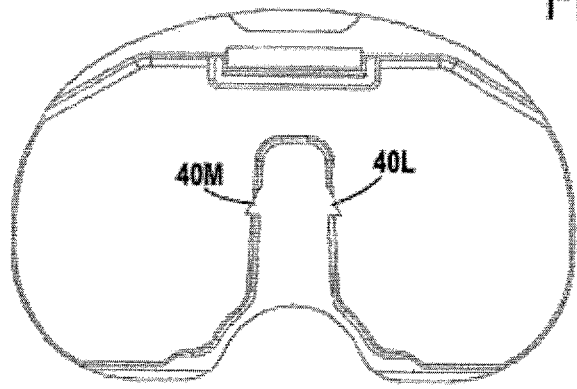
FIG. 8 is a view from below of the insert shown in FIG. 7.

FIGS. 5 and 6 show another possible method of implementation of a tibial plate according to the invention and FIGS. 7 and 8 show another possible method of implementation of an insert according to the invention. Where the elements of the tibial plate and the insert are the same as those in the method of implementation shown in FIGS. 1 and 2, the same numerical references have been used. With respect to the methods of implementation shown in FIGS. 1 and 2, the method of implementation shown in FIGS. 5 and 6 differ in two ways. Each method can be implemented independently to form three distinct methods of implementation, namely a method of implementation that implements one of the differences, another method of implementation that only implements the other difference and a third method of implementation that implements both the differences compared with the method of implementation shown in FIGS. 1 and 2.

The first modification consists in providing two vertical ribs 30L and 30M in the lateral vertical walls 17'L and 17'M of the promontory 14' which work together by snap-fitting into two matching cavities 40L and 40M formed in the vertical wall bounding the cavity 26' in the corresponding tibial insert.

Concerning the shape of the promontory 14', the faces 17'L and 17'M, as shown in FIGS. 5 to 8, may be made parallel, or mutually inclined to give the part forming the promontory the shape of a truncated cone, at least for a segment extending in the sagittal axis, for example from the posterior margin of the plate to the ribs 30M, 30L respectively and/or from the ribs 30M, 30L respectively to the rounded junctions with the face 18 forming the summit.

The other modification consists in implementing the part 4' forming the anterior abutment so that it has a vertical anterior face 7' that extends from one end to the other, in the vertical plane, parallel to the medio-lateral axis, without requiring end parts inclined to a central part.

Figure 9:
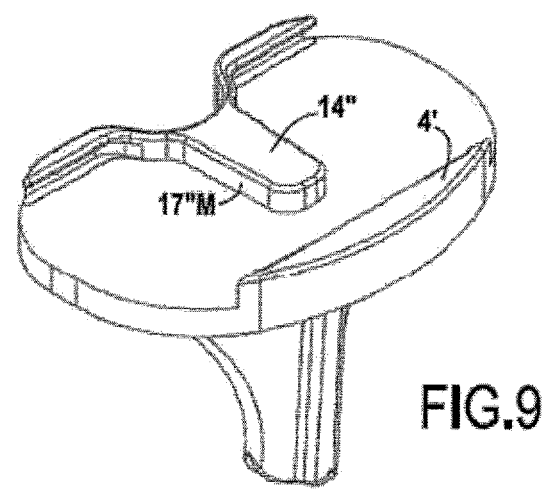
FIG. 9 is a perspective view from above of a third method of implementation of a tibial plate according to the invention.
Figure 10:
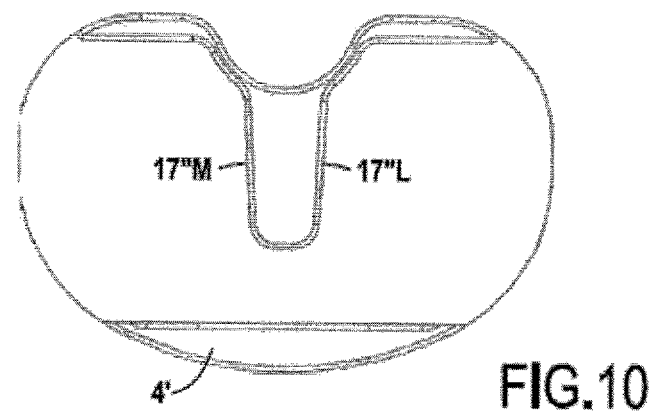
FIG. 10 is a perspective view from above of the tibial plate shown in FIG. 9.

FIGS. 9 and 10 show a method of implementation in which the tibial component is based on the tibial component shown in FIGS. 5 and 6, the only modification being that the part forming the promontory comprises faces 17'''L and 17'''M that are not parallel as in the methods of implementation shown in FIGS. 1 and 2 and 5 and 6, but mutually inclined giving the part 14'' forming the promontory the shape of a truncated cone at least for a segment extending in the sagittal axis, for example from the posterior margin of the plate to the rounded junctions with the face 18 forming the summit.

Figure 11:
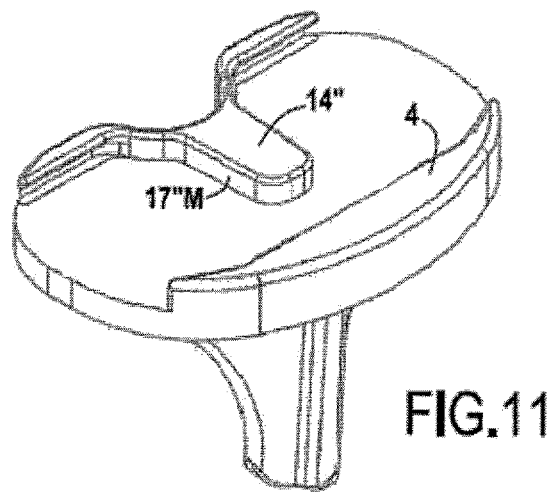
FIG. 11 is a perspective view according to a fourth method of implementation of a tibial plate according to the invention.
Figure 12:
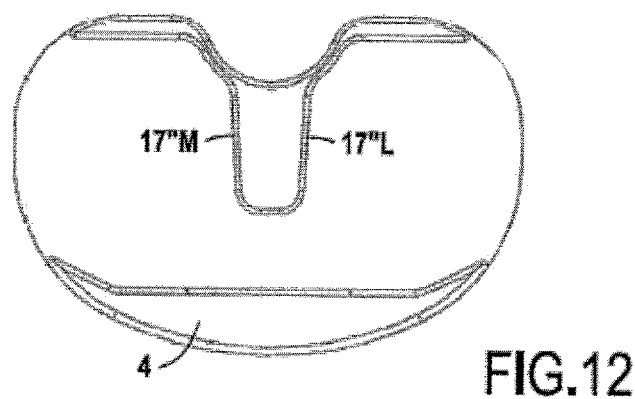
FIG. 12 is a perspective view from above of the tibial plate shown in FIG. 11.
Figure 13:
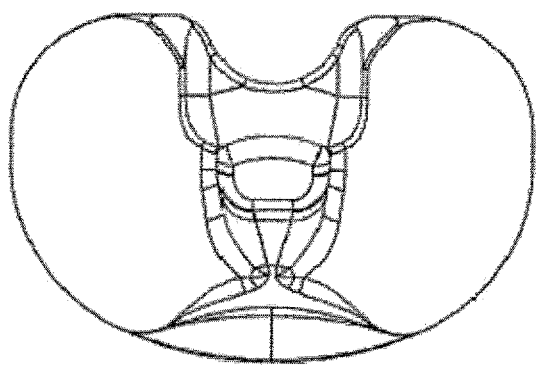
FIG. 13 is a perspective view from above of the tibial insert shown in FIG. 3 or 4.
Figure 14:
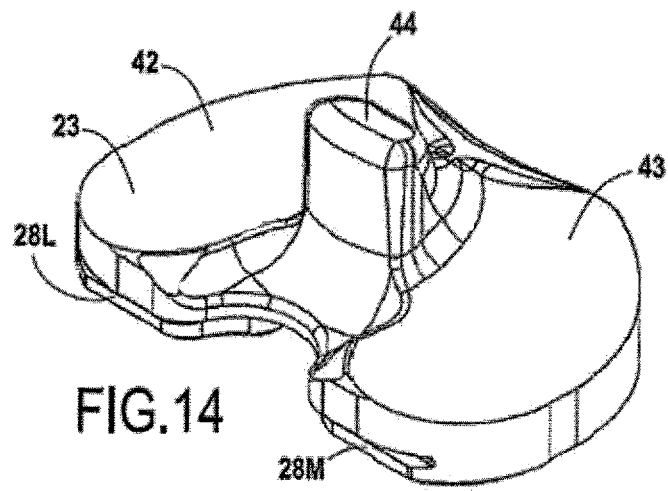
FIG. 14 is a perspective view from above of the tibial insert shown in FIG. 13.
Figure 15:
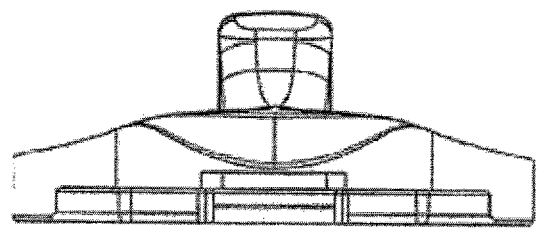
FIG. 15 is a view from the anterior side of the tibial insert shown in FIGS. 13 and 14.
Figure 16:
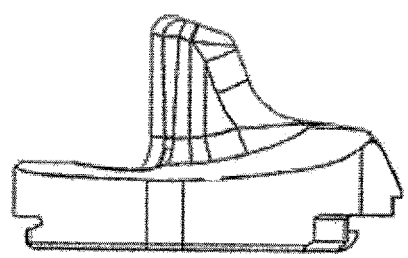
FIG. 16 is a profile view of the tibial insert shown in FIGS. 13 to 15.

FIGS. 11 and 12 show a method of implementation essentially identical to that shown in FIGS. 1 and 2. The only difference consists in a modification of the shape of the part forming the promontory that, in the method of implementation shown in FIGS. 11 and 12, is slightly conical. This means that the lateral walls 17"L and 17"M are not essentially parallel, unlike in the method of implementation shown in FIGS. 1 and 2 but are slightly inclined towards each other, converging in the direction of the anterior abutment. The rest of the method of implementation shown in FIGS. 11 and 12 is identical to that shown in FIGS. 1 and 2. The angle of inclination of the faces 17"L and 17"M may preferably be between 2° and 15°, in particular between 3° and 15°. This modification may also be implemented in the methods of implementation described in FIGS. 5 to 10. The form of the cut-out covering the promontory is consequently modified.

Figure 17:
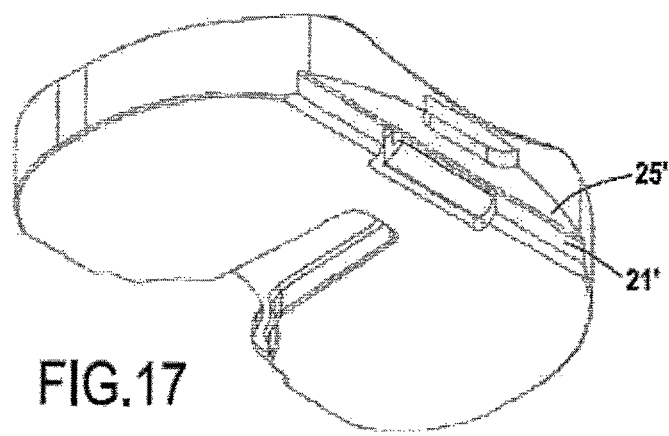
FIG. 17 is a perspective view of a tibial insert designed to work with the tibial plate shown in FIGS. 9 and 10.

FIG. 17 shows a tibial insert designed to work with the tibial plate shown in FIGS. 9 and 10, the insert comprising an anterior cut-out 25' with a shape that matches the anterior abutment 4', the posterior face 21' of the anterior cut-out 25' extending in a vertical plane (with the exception of the tab 29) for all the medio-lateral dimension of the anterior cut-out 25'.

Figure 18:
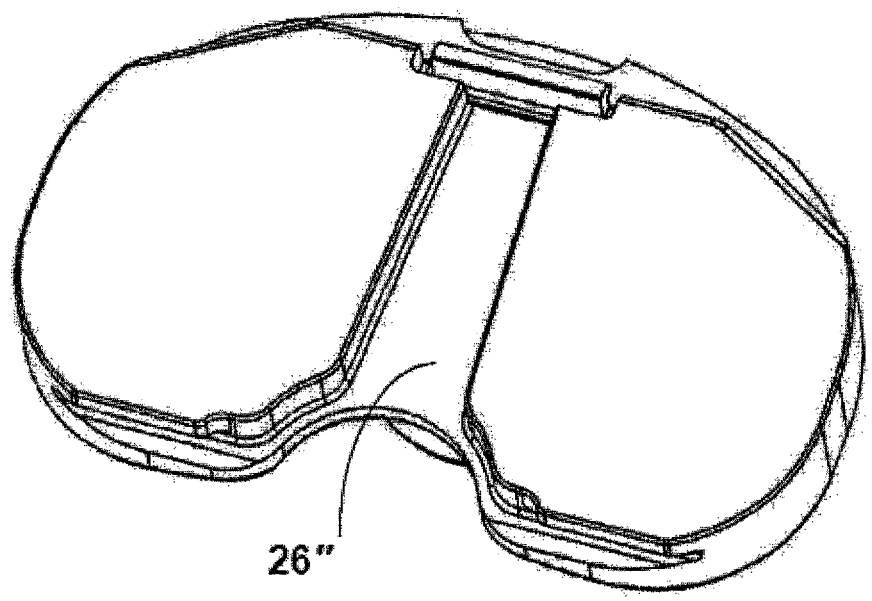
FIG. 18 is a perspective view from above of an insert according to yet another method of implementation that can work with the tibial plate shown in FIG. 11.
Figure 19:
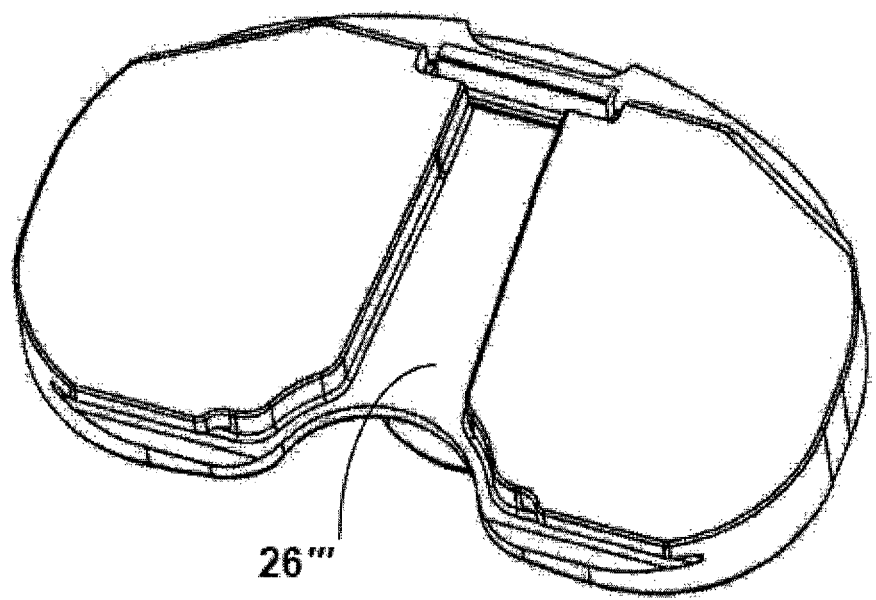
FIG. 19 is a perspective view from above of an insert according to yet another method of implementation that can work with the tibial plate shown in FIG. 11.

FIGS. 18 and 19 show two additional methods of implementation of a tibial insert that can work with the plate shown in FIG. 11. In these two diagrams, the tibial insert is such that the regions 26" and 26"' that cover the part forming the promontory runs through, extending along the antero-posterior axis from the posterior margin up to the tab 29.

In FIG. 18, the region 26" shows its two lateral and medial walls inclined together at the same angle as the inclination between the lateral and medial faces of the part forming the promontory 14", the inclination continuing up to the end of the crossing, that is to say up to the tab 29, while in FIG. 19, the inclination of the lateral and medial walls is only present up to the end of the part forming the promontory 14", the region 26"' having lateral and medial walls parallel beyond the part forming the promontory 14" up to the tab 29.

Finally, FIGS. 13 to 16 show an insert with the method of implementation described in FIGS. 3 and 4 in accordance with the perspective views above, from the front and profile respectively. Below can be seen the two concave upper faces 42 and 43 defined in the upper face 23 and designed to come into contact with the external surfaces of the condyles of the femoral component (not shown in the diagrams), and a central post 44 intended to enter the intercondylar space to provide guidance when flexing the femoral component with respect to the tibial component.

The invention claimed is:

1. A tibial component of a knee prosthesis, comprising a tibial plate having a lower face and an upper face and a tibial insert, the tibial plate further comprising anchoring means projecting from the lower face of the tibial plate, at least two distinct abutments, anterior and posterior respectively, projecting from the upper face of the tibial plate, the anterior abutment extending along at least part of an anterior margin of the tibial plate and the posterior abutment extending along at least part of a posterior margin of the tibial plate and comprising a part forming a promontory extending from the posterior margin in the direction of the anterior abutment in the form of a promontory, and an anterior window shaped cut-out formed in the anterior abutment so as to open onto a posterior face of the anterior abutment opposite the promontory, the tibial insert having an upper face, a lower face and a lateral face, the lateral face comprising an anterior face, a posterior face and two side faces, lateral and medial respectively, a posterior cut-out formed in the lower face of the tibial insert, the posterior cut-out having a shape matching the promontory, characterized in that at least one flexible tab projects from the anterior face of the insert and enters the anterior window shaped cut-out, wherein said window shaped cut out has an upper edge against which said at least one flexible tab bears.

2. A tibial plate for a tibial component of a total knee prosthesis having a lower face and an upper face and comprising anchoring projecting from the lower face, at least two distinct abutments, anterior and posterior respectively, projecting from the upper face, the anterior abutment extending along at least part of an anterior margin of the tibial plate and the posterior abutment extending along at least part of a posterior margin of the tibial plate and comprising a part forming a promontory extending from the posterior margin in the direction of the anterior abutment, and a central, anterior window shaped cut-out formed in the anterior abutment opening onto the posterior face of the anterior abutment opposite the promontory, the part forming the promontory being symmetrical about the Antero-Posterior (AP) or sagittal axis and wherein said window shaped cut-out having an upper edge.

3. The tibial plate according to claim 2, characterized in that the posterior face of the anterior abutment comprises a central section extending in a first plane, and two end sections lateral and medial respectively, that extend in their respective planes, and which form respective angles with respect to the first plane of less than 180°.

4. The tibial plate according to claim 2, characterized in that the promontory has a shape elongated in the sagittal direction, that is to say its greatest dimension in the sagittal or antero-posterior direction is greater than its greatest dimension in the medio-lateral direction, and one or more vertical ribs project from at least one of the lateral faces of the medial and lateral sides of the promontory.

5. The tibial plate according to claim 2, characterized in that the promontory is bounded by a lateral wall defined by two faces, medial and lateral respectively, meeting at an anterior face forming a summit, the faces of the lateral wall being straight, inclined inwards or curved so as not to present upper hooking edges.

6. The tibial plate according to claim 2, characterized in that the promontory has an elongated shape, that is to say its greatest length, that is to say in the Antero-Posterior, or AP direction, is greater than its greatest width, that is to say in the ML, or medio-lateral direction.

7. The tibial plate according to claim 2, characterized in that the promontory is in at least one sagittal segment along the sagittal direction in the shape of a truncated cone, that is to say its width, measured in the medio-lateral direction, decreases along at least one segment facing in the sagittal direction, towards the anterior abutment.

8. The tibial plate according to claim 2, characterized in that the promontory is solid and does not contain a hole to accept a stem projecting from the lower face of the tibial insert.

9. A tibial component comprising a tibial plate according to claim 2.

10. A tibial insert for a tibial component of a knee prosthesis having an upper face, a lower face, and a lateral face, the lateral face comprising an anterior face, a posterior face and two side faces, lateral and medial respectively, a posterior cut-out formed in the lower face, the posterior cut-out being bounded by an anterior face set back with respect to the posterior face of the insert and having a shape matching a promontory, characterized in that at least one flexible tab projects centrally from the anterior side of the insert.

11. The tibial insert according to claim 10, characterized in that it comprises an anterior cut-out formed in the lower face of the insert, on the anterior side, this anterior cut-out being bounded by a posterior face and an upper face, opening on the anterior side and underneath, the posterior face of the anterior cut-out comprising a central section extending in a first plane parallel to the medio-lateral axis, and two end sections, lateral and medial respectively, that extend in their respective planes forming a respective angle with respect to the first plane of greater than 180°.

12. The tibial insert according to claim 10, characterized in that the posterior cut-out with a shape matching the promontory has a shape elongated in the sagittal direction, that is to say that its greatest dimension in the sagittal or antero-posterior direction is greater than its greatest dimension in the medio-lateral direction, and it is formed in the anterior face of the posterior cut-out in the insert, in the matching region of the promontory and the vertical grooves.

13. The tibial insert according to claim 10, characterized in that the posterior cut-out in the insert comprises two faces, medial and lateral respectively, meeting at the anterior face, the medial and lateral faces, and the anterior face of the posterior cut-out in the insert being straight, inclined inwards or curved so as not to present upper hooking edges.

14. The tibial insert according to claim 10, characterized in that the posterior cut-out matching the shape of the promontory has an elongated shape, that is to say that its greatest length, that is to say in the Antero-Posterior, or AP direction, is greater than its greatest width, that is to say in the ML or medio-lateral direction, and symmetrical about the AP axis.

15. The tibial insert according to claim 10, characterized in that the promontory is in at least one sagittal segment along the sagittal direction with the shape of a truncated cone, that is to say its width, measured in the medio-lateral direction, decreases along at least one segment facing in the sagittal direction, towards the anterior abutment.

16. A tibial component comprising a tibial insert according to claim 10.

* * * * *